United States Patent [19]
Reiffenrath et al.

[11] Patent Number: 4,925,590
[45] Date of Patent: May 15, 1990

[54] DERIVATIVES OF 4-CYANO-2,3-DIFLUOROPHENOL

[75] Inventors: Volker Reiffenrath, Rossdorf; Joachim Krause, Dieburg; Andreas Wächtler, Griesheim; Georg Weber, Erzhausen; Ulrich Finkenzeller, Plankstadt, all of Fed. Rep. of Germany

[73] Assignee: Merck Patent Gesellschaft Mit Beschrankter Haftung, Darmstadt, Fed. Rep. of Germany

[21] Appl. No.: 321,045

[22] Filed: Mar. 9, 1989

[30] Foreign Application Priority Data

Mar. 10, 1988 [DE] Fed. Rep. of Germany ....... 3807822

[51] Int. Cl.⁵ .......................... G02F 1/13; C09K 19/30; C09K 19/34; C09K 19/20; C07C 121/75; C07D 319/00; C07D 239/34
[52] U.S. Cl. .............................. 252/299.61; 252/299.5; 252/299.6; 252/299.63; 252/299.64; 252/299.65; 252/299.66; 350/350 R; 350/350 S; 558/414; 558/416; 558/423; 558/425; 544/224; 544/238; 544/295; 544/296; 544/298; 544/316; 544/333; 544/335; 544/336; 544/406; 544/408; 544/410; 546/256; 546/261; 546/263; 546/264; 546/268; 546/278; 546/280; 546/298; 546/300; 546/326; 546/330; 549/21; 549/22; 549/28; 549/13; 549/14; 549/357; 549/370; 549/372; 549/373; 549/378; 549/415; 549/419; 549/425; 549/426; 549/427
[58] Field of Search ....................... 252/299.61, 299.62, 252/299.6, 299.63, 299.64, 299.65, 299.66, 299.5; 350/350 R, 350 S; 558/423, 414, 416, 425; 544/295, 296, 298, 316, 333, 335, 224, 238, 406, 408, 410, 336; 549/22, 21, 415, 370, 28, 419, 372, 13, 425, 373, 14, 426, 378, 357, 427; 546/298, 268, 300, 256, 261, 326, 263, 264, 330, 278, 280

[56] References Cited

U.S. PATENT DOCUMENTS

| 4,602,851 | 7/1986 | Jenner et al. | 252/299.63 |
| 4,659,502 | 4/1987 | Fearon et al. | 252/299.63 |
| 4,664,840 | 5/1987 | Osman | 252/299.63 |
| 4,689,176 | 8/1987 | Inoue et al. | 252/299.65 |
| 4,710,315 | 12/1987 | Schad et al. | 252/299.63 |
| 4,724,097 | 2/1988 | Romer et al. | 252/299.63 |
| 4,776,973 | 10/1988 | Bofinger et al. | 252/299.61 |
| 4,820,839 | 4/1989 | Krause et al. | 252/299.61 |
| 4,834,904 | 5/1989 | Krause et al. | 252/299.61 |

FOREIGN PATENT DOCUMENTS 8802130 3/1988 World Int. Prop. O. ...... 252/299.63

Primary Examiner—Teddy S. Gron
Attorney, Agent, or Firm—Millen, White & Zelano

[57] ABSTRACT

Derivatives of 4-cyano-2,3-difluorophenol of the formula I

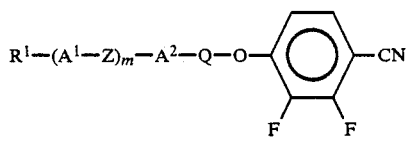

wherein
$R^1$ is an alkyl group which has 1-12 C atoms and in which one or two $CH_2$ groups can also be replaced by —O—, —CO—, —CO—O— and/or —CH=CH—, no two O atoms being directly attached to one another,
$A^1$ and $A^2$ independently of one another are each 1,4-phenylene which is unsubstituted or substituted by one or two F atoms, and in which one or two CH groups can also be replaced by N, or trans-1,4-cyclohexylene in which one or two non-adjacent $CH_2$ groups can also be replaced by O atoms and/or S atoms,
Z is —CO—O—, —O—CO—, —$CH_2CH_2$—, $OCH_2$—, —$CH_2O$, —C≡C— or a single bond,
m is 0, 1 or 2 and
Q is —CO— or —$CH_2$—.

11 Claims, No Drawings

DERIVATIVES OF 4-CYANO-2,3-DIFLUOROPHENOL

CROSS-REFERENCE TO RELATED APPLICATIONS

This application is related to commonly assigned U.S. application Ser. Nos. 07/321,426; 07/321,427; and 321,428, each filed Mar. 9, 1989, each of which is entirely incorporated by reference herein.

SUMMARY OF THE INVENTION

The invention relates to derivatives of 4-cyano-2,3-difluorophenol of the formula I

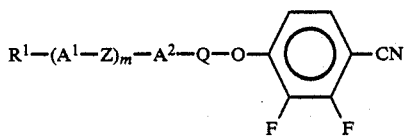

wherein $R^1$ is an alkyl group which has 1-12C atoms and in which one or two $CH_2$ groups can also be replaced by —O—, —CO—, —CO—O— and/or —CH=CH—, no two O atoms being directly attached to one another, $A^1$ and $A^2$ independently of one another are each 1,4-phenylene which is unsubstituted or substituted by one or two F atoms, and in which one or two CH groups can also be replaced by N, or trans-1,4-cyclohexylene in which one or two non-adjacent $CH_2$ groups can also be replaced by O atoms and/or S atoms, Z is —CO—O—, —O—CO—, —$CH_2CH_2$—, $OCH_2$—, —$CH_2O$—, —C≡C— or a single bond, m is 0, 1 or 2 and Q is —CO— or —$CH_2$—.

For the sake of simplicity, in the following text Cyc is a 1,4-cyclohexylene group, Dio is a 1,3-dioxane-2,5-diyl group, Dit is a 1,3-dithiane-2,5-diyl group, Phe is a 1,4-phenylene group, Pyd is a pyridine-2,5-diyl group, Pyr is a pyrimidine-2,5-diyl group and Pyn is a pyridazine-2,5-diyl group. Phex is a group of the formula

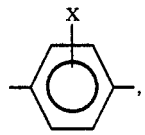

X in the following text being preferably chlorine or fluorine.

PF2N is a group of the formula

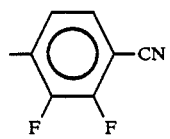

The compounds of the formula I can be used as components of liquid-crystal phases, in particular for displays based on the principle of the twisted cell, the guest-host effect, the effect of the deformation of aligned phases or the effect of dynamic scattering.

An important criterion for the multiplex operation of such cells is a low ratio of the anisotropy of the dielectric constant to the dielectric constant perpendicular to the axis of the molecule, i.e. of $\Delta\epsilon/\epsilon\perp$ (cf., for example, Gharadjedagji, F. et al., Rev. Phys. Appl. Nos. 11, 1976 (467)).

In order to obtain a low $\Delta\epsilon/\epsilon\perp$, it is conventional practice to mix substances having a negative $\Delta\epsilon$ with substances having a positive $\Delta\epsilon$.

However, it is better to employ substances which have a strong transverse dipole in addition to a positive $\Delta\epsilon$. A number of liquid-crystal compounds of this type have already been synthesized at the present time, for example carboxylic acid esters of 4-cyano-2(3)-fluorophenol or 5-cyanopyridin-2-yl compounds.

In general, however, the latter exhibit disadvantages, such as, for example, poor solubility in mixtures, high viscosity, high melting points and instability to chemicals. In addition, they possess, as a rule, a strong tendency to form smectic phases of a fairly high order. There is, therefore, a need for further compounds having positive dielectric anisotropy and, at the same time, a high dielectric constant perpendicular to the axis of the molecule which make it possible to improve further the properties of mixtures for a very wide variety of electro-optical applications.

The invention provides stable, liquid-crystal or mesogenic compounds having a positive dielectric anisotropy, a large negative transverse dipole and, at the same time, a low viscosity.

It has been found that the compounds of the formula I are excellently suitable for use as components of liquid-crystal phases. In particular, stable, liquid-crystal phases having a broad mesophase range and a comparatively low viscosity can be prepared with their aid.

In addition, the range of liquid-crystal substances which are suitable from various aspects of technical performance for the preparation of liquid-crystal mixtures is considerably broadened, in a very general way, by the provision of the compounds of the formula I.

The compounds of the formula I possess a wide range of applications. Depending on the choice of substituents, these compounds can be used as the base materials of which liquid-crystal phases are predominantly composed; it is also possible, however, to add compounds of the formula I to liquid-crystal base materials belonging to other classes of compounds in order, for example, to vary the dielectric and/or optical anisotropy and/or the viscosity and/or the spontaneous polarization and/or the phase ranges and/or the tilt angle and/or the pitch of such a dielectric.

The compounds of the formula I are also suitable for use as intermediates for the preparation of other substances which can be used as constituents of liquid-crystal dielectrics.

The compounds of the formula I are colorless in the pure state and form liquid-crystal mesophases within a temperature range which is advantageously situated for electrooptical use. They are very stable to chemicals, heat and light.

The invention therefore relates to the compounds of the formula I and to 4-cyano-2,3-difluorophenol as an intermediate product in the synthesis of compounds of the formula I.

The invention also relates to the use of the compounds of the formula I as components of liquid-crystal phases. The invention also relates to liquid-crystal phases containing at least one compound containing a 4-cyano-2,3-difluorophenoxy group as a structural element, in particular a compound of the formula I, and to liquid-crystal display elements containing phases of this type. Phases of this type have particularly advantages elastic constants and, because of their low $\Delta\epsilon/\epsilon\perp$ values, are particularly suitable for TFT mixtures.

In the preceeding and following text $R^1$, $A^1$, $A^2$, Z and m have the meaning indicated, unless anything contrary is expressly noted.

Accordingly, the compounds of the formula I embrace compounds having two rings of the partial formulae Ia and Ib:

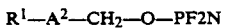  Ia

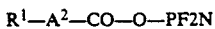  Ib, compounds having three rings of the partial formulae Ic and Id:

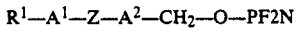  Ic

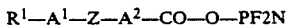  Id, compounds having four rings of the partial formulae Ie and If:

  Ie

  If and compounds having five rings of the partial formulae Ig and Ih:

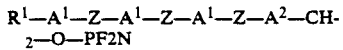  Ig
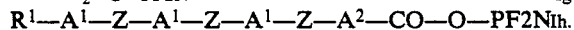  Ih.

In the compounds of the preceeding and following formulae $R^1$ is preferably alkyl, and also alkoxy. $A^1$ and $A^2$ are preferably Phex, Cyc, Phe, Dio or Pyr; the compound of the formula I preferably does contain more than one of the radicals Dio, Dit, Pip, Bi, Pyn, Pyr or Phex in each case.

m is preferably 0, 1 or 2, particularly preferably 1.

The groups Z, which can be identical and different, are preferably single bonds or, as a second preference, a —CO—O—, —O—CO—, —C≡C— or —CH₂CH₂— group. Compounds of the formula I wherein all the groups Z are single bonds or one group Z is —CO—O—, —O—CO—, —C≡C— or —CH₂CH₂— are particularly preferred.

In the preceding and following formulae $R^1$ preferably has 2–10 C atoms, in particular 3–7 C atoms. It is also possible for one or two CH₂ groups in $R^1$ to be replaced. Preferably, only one CH₂ group is replaced by —O—, —CO—, —C≡C—, —S—, —CH═CH—, —CH—halogen or —CHCN—, in particularly by —O—, —CO— or —C≡C—.

Halogen is F, Cl, Br or I, preferably Cl.

In the preceding and following formulae $R^1$ is preferably alkyl, alkoxy or another oxaalkyl group, and also alkyl groups in which one or more CH₂ groups can be replaced by a grouping selected from the group composed of —O—, —O—CO—, —C≡C—, —CH═CH—, —CH—halogen— and —CHCN— or by a combination of two suitable groupings, no two heteroatoms being directly attached to one another.

If $R^1$ is an alkyl radical in which one ("alkoxy" or "oxaalkyl") group or two non-adjacent ("alkoxyalkoxy" or "dioxaalkyl") CH₂ groups can be replaced by O atoms, it can be linear or branched. Preferably, it is linear and has 2, 3, 4, 5, 6 or 7 C atoms and is, accordingly, preferably ethyl, propyl, butyl, pentyl, hexyl, heptyl, ethoxy, propoxy, butoxy, pentoxy, hexyloxy or heptyloxy, and also methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl is preferably linear 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,5- or 3,5-dioxahexyl, or 1,3-, 1,4-, 1,5-, 1,6-, 2,4-, 2,5-, 2,6-, 3,6- or 4,6-dioxaheptyl.

If $R^1$ is an alkyl radical in which a CH₂ group has been replaced by —CH═CH— it can be linear or branched. Preferably, it is linear and has 2 to 10 C atoms. Accordingly, it is especially vinyl, prop-1-2-enyl, but-1, -2- or -3-enyl, pent-1-, -2-, -3- or -4-enyl, hex-1, -2-, -3-, -4- or -5-enyl, hept-1-, -2-, -3-, 4-, -5- or -6-enyl, oct-1-, -2-, -3-, -4-, 5-, -6- or -7-enyl, non-1-, -2-, -3-, -4-, -5-, -6-, -, -7- or -8-enyl or dec-1-, -2-, -3-, -4-, -5-, -6-, -7-, -8- or -9-enyl.

If $R^1$ is an alkyl radical in which a CH₂ group has been replaced by —O—CO—, or —CO—O—, this radical can be linear or branched. Preferably, it is linear and has 2 to 6 C atoms. Accordingly, it is especially acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)-ethyl, 2-(ethoxycarbonyl)-ethyl, 2-(propoxycarbonyl)-ethyl, 3-(methoxycarbonyl)-propyl, 3-(ethoxycarbonyl)-propyl and 4-(methoxycarbonyl)-butyl.

Compounds of the formula I having a branched wing group $R^1$ can, occasionally, be of importance owing to improved solubility in the customary liquid-crystal base materials, but are particularly of importance as chiral doping agents, if they are optionally active. Smetic compounds of this type are suitable for uses as components of ferroelectric materials.

As a rule, branched groups this type do not contain more than one chain branching. Preferred branched radicals $R^1$ are isopropyl, 2-butyl (=methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4- methylvaleryloxy, 2-chloro-3-methylvaleryloxy, 2-methyl-3-oxapentyl and 2-methyl-3-oxahexyl.

If $R^1$ is an alkyl radical in which two or more $CH_2$ groups have been replaced by —O— and/or —CO—O—, this radical can be linear or branched. Preferably, it is branched and has 3 to 12 C atoms. Accordingly, it is especially bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carbonyl-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl) -pentyl, 6,6-bis-(methoxycarbonyl)-hexyl, 7,7-bis-(methoxycarbonyl) -heptyl, 8,8-bis-(methoxycarbonyl)-octyl, bis-(ethoxycarbonyl)-ethyl, 3,3-bis-(ethoxycarbonyl)-propyl, 4,4-bis-(ethoxycarbonyl) -butyl, 5,5-bis-(ethoxycarbonyl)-pentyl.

Compounds of the formula I provided with wing groups $R^1$ which are suitable for polycondensation reactions are suitable for the preparation of liquid-crystal polycondensates.

Formula I embraces both the racemates of these compounds and the optical antipodes as well as mixtures thereof.

Amongst the compounds of the formulae I and Ia to Ih, preferred compounds are those in which at least one of the radicals contained therein has one of the preferred meanings indicated.

Of the dinuclear compounds of the partial formulae Ia to Ib those of the partial formulae Iaa to Iae and Iba to Ibd are preferred:

| | |
|---|---|
| $R^1$—Phe—$CH_2$—O—P2FN | Iaa |
| $R^1$—Cyc—$CH_2$—O—P2FN | Iab |
| $R^1$—Dio—$CH_2$—O—P2FN | Iac |
| $R^1$—Pyr—$CH_2$—O—P2FN | Iad |
| $R^1$—PheX—$CH_2$—O—P2FN | Iae |
| $R^1$—PheX—CO—O—P2FN | Iba |
| $R^1$—Phe—CO—O—P2FN | Ibb |
| $R^1$—Cyc—CO—O—P2FN | Ibc |
| $R^1$—Pyr—CO—O—P2FN | Ibd |

Of the trinuclear compounds of the partial formula Ic and Id those of the partial formulae Ica to Idm are preferred:

| | |
|---|---|
| $R^1$—Phe—Phe—$CH_2$—O—PF2N | Ica |
| $R^1$—PheX—Phe—$CH_2$—O—PF2N | Icb |
| $R^1$—Phe—PheX—$CH_2$—O—PF2N | Icc |
| $R^1$—Phe—Cyc—$CH_2$—O—PF2N | Icd |
| $R^1$—Cyc—Cyc—$CH_2$—O—PF2N | Ice |
| $R^1$—Cyc—Phe—$CH_2$—O—PF2N | Icf |
| $R^1$—Pyr—Cyc—$CH_2$—O—PF2N | Icg |
| $R^1$—Phe—CO—O—Phe—$CH_2$—O—PF2N | Ich |
| $R^1$—Cyc—CO—O—Phe—$CH_2$—O—PF2N | Ici |
| $R^1$—Cyc—$CH_2CH_2$—Phe—$CH_2$—O—PF2N | Icj |
| $R^1$—Phe—$CH_2CH_2$—Phe—$CH_2$—O—PF2N | Ick |
| $R^1$—Phe—C≡C—Phe—$CH_2$—O—PF2N | Icl |
| $R^1$—Phe—Phe—CO—O—PF2N | Ida |
| $R^1$—Phe—Phe—CO—O—PF2N | Idb |
| $R^1$—Phe—PheX—CO—O—PF2N | Idc |
| $R^1$—Phe—Cyc—CO—O—PF2N | Idd |
| $R^1$—Cyc—Cyc—CO—O—PF2N | Ide |
| $R^1$—Cyc—Phe—CO—O—PF2N | Idf |
| $R^1$—Pyr—Phe—CO—O—PF2N | Idg |
| $R^1$—Phe—O—CO—Phe—CO—O—PF2N | Idh |
| $R^1$—Cyc—O—CO—Phe—CO—O—PF2N | Idi |
| $R^1$—Cyc—CO—O—Phe—CO—O—PF2N | Idj |
| $R^1$—Phe—CO—O—Phe—CO—O—PF2N | Idk |
| $R^1$—Phe—CO—O—Cyc—CO—O—PF2N | Idl |
| $R^1$—Phe—O—CO—Cyc—CO—O—PF2N | Idm |

Of the tetranuclear compounds of the partial formulae Ie to If those of the partial formula I1 to I8 are preferred:

| | |
|---|---|
| $R^1$—$A^1$—$A^1$—$A^2$—$CH_2$—O—PF2N | I1 |
| $R^1$—$A^1$—$A^1$—$A^2$—CO—O—PF2N | I2 |
| $R^1$—$A^1$—$A^1$—$A^2$—CO—O—PF2N | I2 |
| $R^1$—$A^1$—Z—$A^1$—$A^2$—CO—O—PF2N | I3 |
| $R^1$—$A^1$—Z—$A^1$—$A^2$—O—PF2N | I4 |
| $R^1$—$A^1$—$A^1$—Z—$A^2$—$CH_2$—O—PF2N | I5 |
| $R^1$—$A^1$—$A^1$—Z—$A^2$—CO—O—PF2N | I6 |
| $R^1$—$A^1$—Z—$A^1$—Z—$A^2$—CO—O—PF2N | I7 |
| $R^1$—$A^1$—Z—$A^1$—Z—$A^2$—$CH_2$—O—PF2N | I8 |

In the above compounds of the partial formulae I1 to I8 the groups $A^1$ and $A^2$ are preferably trans-1,4-cyclohexylene (Cyc), 1,4-phenylene (Phe), 2-halogeno-1,4-phenylene or 3-halogeno-1,4-phenylene (PheX), dioxane-2,5-diyl (Dio), dithiane-2,5-diyl (Dit) or pyrimidine-2,5-diyl (Pyr). Those of the formulae mentioned above which contain one or more groups Dio, Dit and/or Pyr embrace in each case the two possible 2,5-(Dio, Dit, or Pyr)-position isomers.

The compounds of the formula I are prepared by methods known per se, such as are described in the literature (for example in the standard works such as HoubenWeyl, Methoden der Organischen Chemie ("Methods of Organic Chemistry"), Georg-Thieme-Verlag, Stuttgart), in particular under reaction conditions which are known and suitable for the reactions mentioned. Moreover, it is also possible to make use of variants which are known per se but are not mentioned here in detail.

The starting materials can, if desired, also be formed in situ, by processes in which they are not isolated from the reaction mixture, but are immediately reacted further to give the compounds of the formula I.

Compounds of the formula I are preferably accessible by esterifying or etherifying 4-cyano-2,3-difluorophenol.

The latter is obtained in accordance with known processes by dehydrating the amide of 4-hydroxy-2,3-difluorobenzoic acid. This acid is prepared by carboxylating, with carbon dioxide, 4-trimethylsiloxy-2,3-difluorophenyllithium or 4-alkoxy-2,3-difluorophenyllithium, which is produced analogously to known methods (for example A.M. Roe et al., J. Chem. Soc. Chem. Comm. 22, 582 (1965)).

Furthermore, 4-trimethylsiloxy-2,3-difluorobenzaldehyde or 4-alkoxy-2,3-difluorobenzaldehyde (obtainable from the lithium compound by formylation with formamides) can readily be converted into the nitrile (for example J. Streith et al. Helv. Chim. Acta 59, 2786 (1976)).

A further possible means of preparing 4-cyano-2,3-difluorophenol is the reaction of 4-trimethylsiloxy-2,3-difluorophenyllithium with cyanogen chloride or bromide.

Finally, 4-cyano-2,3-fluorophenol can be obtained from 2,3-difluoro-4-methoxynitrobenzene (prepared, for example, by the method of R. Bolton et al., J. Chem. Soc. Perkin II, 1978, 141) by reduction, diazotization, reaction with $Cu_2(CN)_2$ and subsequent ether cleavage.

The compounds of the formula I can also be prepared by reducing a compound which otherwise corresponds to the formula I, but contains one or more reducible groups and/or C—C bonds instead of H atoms.

Suitable reducible groups are preferably carbonyl groups, in particular keto groups, and also, for example, free or esterified hydroxyl groups or halogen atoms attached to an aromatic nucleus. Preferred starting materials for the reduction correspond to the formula I, but can contain a cyclohexene ring or cyclohexanone ring instead of a cyclohexane ring and/or a —CH=CH— group instead of a —$CH_2CH_2$— group and/or a —CO— group instead of a —$CH_2$— group and/or a free or functionally modified (for example in the form of its p-toluenesulfonate) OH group instead of an H atom.

The reduction can, for example, be effected by catalytic hydrogenation at temperatures between about 0° C. and about 200° C. and under pressures between about 1 and 200 bar, in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example $PtO_2$ or PdO), on a support (for example Pd on charcoal, calcium carbonate or strontium carbonate) or in a finely divided form.

Ketones can also be reduced by the methods of Clemmensen (using zinc, amalgamated zinc or tin and hydrochloric acid, preferably in an aqueous-alcoholic solution or in a heterogeneous phase with water/toluene at temperatures between about 80° and 120°) or Wolff-Kishner (using hydrazine, preferably in the presence of an alkali, such as KOH or NaOH, in a high-boiling solvent, such as diethylene glycol or triethylene glycol, at temperatures between about 100° and 200°) to give the corresponding compounds of the formula I containing alkyl groups and/or —$CH_2CH_2$— bridges.

Reductions by means of complex hydrides are also possible. For example, arylsulfonyloxy groups can be removed reductively by means of $LiALH_4$, in particular p-toluenesulfonyloxymethyl groups can be reduced to methyl groups, preferably in an inert solvent, such as diethyl ether or THF temperatures between about 0° and 100°. Double bonds can be hydrogenated (even in the presence of CN groups) by means of $NaBH_4$ or tributyltin hydride in methanol.

Esters of the formula I can also be obtained by esterifying corresponding carboxylic acids (or reactive derivatives thereof) with alcohols or phenols (or reactive derivatives thereof).

Suitable reactive derivatives of the carboxylic acids mentioned are, in particular, the acid halides, above all the chlorides and bromides, and also the anhydrides, for example also mixed anhydrides, azides or esters, in particular alkyl esters having 1-4 C atoms in the alkyl group.

Suitable reactive derivatives of the alcohols or phenols mentioned are, in particular, the corresponding metal alcoholates or phenates, respectively, preferably of an alkali metal such as Na or K.

The esterification is advantageously carried out in the presence of an inert solvent. Solvents which are very suitable are, in particular, ethers, such as diethyl ether, di-n-butyl ether, THF, dioxan or anisole, ketones, such as acetone, butanone or cyclohexanone, amides, such as DMF or hexamethylphosphoric triamide, hydrocarbons, such as benzene, toluene or xylene, hologenated hydrocarbons, such as carbon tetrachloride or tetrachloroethylene, and sulfoxides, such as dimethyl sulfoxide, or sulfolane. Water-immiscible solvents can, at the same time, be used advantageously to remove by azeotropic distillation the water formed in the course of the esterification. Occasionally, it is also possible to use an excess of an organic base, for example pyridine, quinoline or triethylamine, as the solvent for the esterification. The esterification can also be carried out in the absence of a solvent, for example merely by heating the components in the presence of sodium acetate. The reaction temperature is usually between −50° and +250°, preferably between −20° and +80°. At these temperatures the esterification reactions are, as a rule, complete after 15 minutes to 48 hours.

A further preferred process for the preparation of the esters is to react a carboxylic acid with an alcohol or phenol in the presence of a dehydrating agent, if appropriate using an organic base as catalyst.

Dehydrating agents which are particularly preferred are molucular sieves or carbodiimides, such as, for example, dicyclohexylcarbodiimides. A particularly suitable basic catalyst is 4-dimethylaminopyridine.

In an individual case the reaction conditions for the esterification depend largely on the nature of the starting materials used. Thus a free carboxylic acid will, as a rule, be reacted with a free alcohol or phenol in the presence of a strong acid, for example a mineral acid, such as hydrochloric acid or sulfuric acid. A preferred procedure is to react an acid anhydride or, in particular, an acid chloride with an alcohol, preferably in a basic medium, bases of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification consists in first converting the alcohol or the phenol into the sodium or potassium alocholate or phenate, respectively, for example by treatment with ethanolic sodium hydroxide or ptoassium hydroxide solution, isolating this alcohlate or phenate and suspending it, with stirring, in acetone or diethyl ether together with sodium bicarbonate or potassium carbonate, and adding a solution of the acid chloride or anhydride in diethyl ether, acetone or DMF to this suspension, preferably at temperatures between about −25° and +20°.

Corresponding acid amides can be dehydrated in order to prepare nitriles of the formula I. The amides can be obtained, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2Cl_2$, $COCl_2$ and also $P_2O_5$, $P_2S_5$ and $AlCl_3$ (for example as the double compound with NaCl), and aromatic sulfonic acids and sulfonic acid halides. This reaction can be carried out in the presence or absence of an inert solvent at temperatures between about 0° and 150°; examples of suitable solventgs are bases, such as pyridine or triethylamine, aromatic hydrocarbons such as benzene, toluene or xylene, or amides, such as DMF.

The abovementioned nitriles of the formula I can also be prepared by reacting corresponding acid halides, preferably the chlorides, with sulfamide, preferably in an inert solvent, such as tetramethylene sulfone, at temperatures between about 80° and 150°, preferably at 120°. After working up in the customary manner, the nitriles can be isolated without further treatment.

Compounds of the formula I can also be obtained from the corresponding diazonium salts by replacing the diazonium group by a CN group, for example using the Sandmeyer method.

The diazonium salts can be prepared, for example, by nitrating compounds which correspond to the formula I, but contain a hydrogen atom instead of the CN group, reducing the product to give the corresponding amines, and diazotizing the latter, for example, by means of $NaNO_2$ or $KNO_2$, in aqueous solution at temperatures between about −10° and +10°.

Replacement by CN is preferably effected by reacting the aqueous diazonium salt solution with $Cu_2(CN)_2$ by the Sandmeyer method.

The compounds of the formula I can also be prepared by deprotonating, in accordance with methods known per se, compounds which correspond to the formula I, but contain a hydrogen atom instead of the CN group, and subsequently reacting the product with cyanogen chloride or bromide.

The preparation of the toluenes (Z=—C≡C—) is effected, for example, by reacting the corresponding halogen compound with an acetylide in a basis solvent with transition metal catalysis; it is preferable to use palladium catalysts here, in particular a mixture of bis(-triphenylphosphine)-palladium(II) chloride and copper iodide in piperidine as solvent.

Ethers of the formula I can be obtained by etherifying correspondding hydroxy compounds, preferably corresponding phenols, it being preferable first to convert the hydroxy compound into a corresponding metal derivative, for example into the corresponding alkali metal alcoholate or alkali metal phenate by treatment with NaH, $NaNH_2$, NaOH, KOH, $Na_2CO_3$ or $K_2CO_3$. This alcoholate or phenate can then be reacted with the corresponding alkyl halide or sulfonate or dialkyl sulfate, preferably in an inert solvent, such as acetone, 1,2-dimethoxyethane, DMF or dimethyl sulfoxide, or an excess of aqueous or aqueous-alcoholic NaOH or KOH, at temperatures between about 20° and 100°.

In addition to one or more compounds according to the invention, the liquid-crystal phases according to the invention preferably contain, as further constituents, 2 to 40, especially 4 to 30, components. These phases very particularly preferably contain 7 to 25 components as well as one or more compounds according to the invention. These further constituents are preferably selected from nematic or nematogenic (monotropic or isotropic) substances, in particular substances belonging to the clases of azoxybenzenes, benylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoates, cyclohexylphenylcyclohexanecarboxylates, cyclohexylphenylcyclohexylcyclohexanecarboxylates, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylpiphenyls, phenylpyrimidines, cyclohexylpyrimidines, phenylpyridines, cyclohexylpyridines, phenyldioxanes, cyclohexyldioxanes, phenyl-1,3-dithianes, cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)-ethanes, 1-cyclohexyl-2-biphenylylethanes, 1-phenyl-2-cyclohexylphenylethanes, optionally halogenated stilbenes, benzyl pehnyl ethers, tolanes and substituted cinnamic acids. The 1,4-phenylene groups in these compounds can also be fluorinated.

The most important compounds which are suitable for use as further constituents of phases according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH₂CH₂—E—R" | 4 |
| R'—L—C≡C—E—R" | 5 |

Inthe formulae, 1, 2, 3, 4 and 5 L and E, which can be identical or different, independently of one another are each a divalent radical belonging to the group conposed of -Phe-, Cyc-, Phe-Phe-, -Phe-Cyc-, -Cyc-Cyc-, -Pyr-, -Dio-, -G-Phe- and -G-Cyc- and mirror images thereof, Phe being 1,4-phenylene which is unsubstituted or substituted by fluorine, Cyc being trans-1,4-cyclohexylene or 1,4-cyclohexenylene, Pyr being pyrimidine-2,5-diyl or pyridine-2,5diyl, Dio being 1,3-dioxane-2,5-diyl and G being 2-(trans-1,4-cyclohexyl)-ethyl, pyrimidine-2,5-diyl, pyridine-2,5-diyl or 1,3-dioxane-2,5-diyl.

Preferably, one of the radicals L and E is Cyc, Phe or Pyr. E is preferably Cyc, Phe or Phe-Cyc. The media according to the invention preferably contain one or more components selected from the compounds of the formulae 1, 2, 3, 4 and 5 wherein L and E are selected from the group composed of Cyc, Phe and Pyr and, at the same time, one or more components selected from the compounds of the formulae 1, 2, 3, 4 and 5 wherein one of the radicals L and E is selected from the group composed of Cyc, Phe and Oyr and the other radical is selected form the group composed of -Phe-Phe-, -Phe-Cyc-, -Cyc-Cyc-, -G-Phe- and -G-Cyc-, and, if appropraite, one or more components selected from the compounds of the formulae 1, 2, 3, 4 and 5 wherein the radicals L and E are selected from the group composed of -Phe-Cyc-, -Cyc-Cyc-, -G-Phe-and -G-Cyc-.

In the compounds of the partial formulae 1a, 2a, 3a, 4aand 5a R' and R" independently of one another are each alkyl, alkenyl, alkoxy, alkenyloxy or alkanoyloxy having up to 8 carbon atoms. In the case of most of these compounds R' and R" are different from one another, one of these radicals being in most cases alkyl or alkenyl. In the compounds of the partial formulae 1b, 2b, 3b, 4b and 5b R" is —CN, —CF$_3$, F, Cl or —NCS; in this connection R has the meaning indicated for the compounds of the partial formulae 1a to 5a and is preferably alkyl or alkenyl. Other variants of the substituents envisaged are also customary in the compounds of the formulae 1, 2, 3, 4 and 5, however. Many substances of this type or mixtures thereof are commerically available. All these substances are obtainable by methods known from the literature or by analogy thereto.

In addition to components from the group composed of the compounds 1a, 2a, 3a, 4a and 5a (group 1), the phases according to the invention also preferably contain components from the group composed of the compounds 1b, 2b, 3b, 4b and 5b (group 2), the proportions thereof being preferably as follows:

Group 1: 20 to 90%, especially 30 to 90%,
Group 2: 10 to 80%, especially 10 to 50%,
the sum of the proportions of the compounds according to the invention and the compounds from groups 1 and 2 adding up to 100%.

The phases according to the invention preferably contain 1 to 40%, in particular preferably 5 to 30%, of compounds according to the invention. Phases containing more than 40%, especially 45 to 90%, of compounds according to the invention are also preferred. The phases preferably contain three, four or five compounds according to the invention.

The preparation of the phases according to the invention is effected in a manner customary per se. As a rule, the components are dissolved in one another, preferably at an elevated temperature. The liquid-crystal phases according to the invention can be modified by means of suitable additives so that they can be used in all types of liquid-crystal display elements hitherto disclosed. Additives of this type are known to those skilled in the art and are described in detail in the literature (H. Kelker/R. Hatz, Handbook of Liquid Crystals, Verlag Chemie, Weinheim, 1980). For example, it is possible to add pleochroic dyestuffs for the production of colored guest-host systems, or substances for modifying the dielectric anisotropy, the viscosity and/or the orientation of the nematic phases.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, are hereby incorporated by reference.

"Customary working up" means as follows: water is added, the mixture is extracted with methylene chloride, the phases are separated, the organic phase is dried and evaporated and the product is purified by crystallization and/or chromatography.

In addition: C is crystalline-solid state, S is smectic phase (the index characterizes the type of phase, N is nematic state, Ch is cholesteric phase and I is isotropic phase. The number between two symbols indicates the transition temperature in degrees centigrade.

EXAMPLES

EXAMPLE 1

Preparation of 2,3-difluoro-4-cyanophenol (a) 4-Ethoxy-2,3-difluorobenzaldehyde 125 ml of a solution of 0.2 mole of n-butyllithium in hexane is added, at −78° C., to a mixture of 0.2 mole of 2,3-difluorophenetole, 0.2 mole of tetramethylethylenediamine and 400 ml of tetrahydrofuran, and the mixture is stirred for 2 hours at −60° C. A mixture of 0.2 mole of n-formylpiperidine and 20 ml of tetrahydrofuran is added dropwise to this mixture. Warming to −20° C. and working up in the customary manner gives the aldehyde in the form of a colourless solid, melting point 70° C.

(b) 4-Ethoxy-2,3-difluorobenzonitrile

A mixture of 0.12 mole of hydroxylamine-0-sulfonic acid and 50 ml of water is added, at 30° C., to a mixture of 0.1 mole of 4-ethoxy-2,3-difluorobenzaldehyde and 100 ml of water, and the mixture is stirred for one hour. Warming to 65° C. for 2 hours and working up in the customary manner gives the nitrile in the form of a colourless solid, melting point 45° C.

(c) 2,3-Difluoro-4-cyanophenol

A mixture of 0.1 mole of 4-ethoxy-2,3-difluorobenzonitrile, 0.12 mole of aluminium chloride and 150 ml of toluene is heated at the boil for 2 hours. Working up in the customary manner gives the phenol in the form of a colourless solid.

EXAMPLE 2

Preparation of 4-aroyloxy-2,3-difluorobenzonitriles

A mixture of 0.11 mole of dicyclohexylcarbodimide and 20 ml of toluene is added to a mixture of 0.1 mole of p-pentylbenzoic acid, 0.1 mole of 2,3-difluoro-4-cyanophenol (prepared as in Example 1), 1.5 g of 4-N,N-dimethylaminopyridine and 200 ml of toluene. After stirring for 4 hours at room temperature 0.4 g of oxalic acid is added to the mixture and stirring is continued for 30 minutes. Working up i the customary manner gives 4-(4-penylbenzoyloxy)-2,3-difluorobenzonitrile.

The following are prepared analogously:
4-(4-Ethylbenzoyloxy)-2,3-difluorobenzonitrile
4-(4-Propylbenzoyloxy)-2,3-difluorobenzonitrile
4-(4-Butylbenzoyloxy)-2,3-difluorobenzonitrile
4-(4-Hexylbenzoyloxy)-2,3-difluorobenzonitrile
4-(4-Heptylbenzoyloxy)-2,3-difluorobenzonitrile 4-(4-Octylbenzoyloxy)-2,3-difluorobenzonitrile
4-(4-Ethoxybenzoyloxy)-2,3-difluorobenzonitrile
4-(4-Propoxybenzoyloxy)-2,3-difluorobenzonitrile
4-(4-Butoxybenzoyloxy)-2,3-difluorobenzonitrile
4-(4-Pentoxybenzoyloxy)-2,3-difluorobenzonitrile
4-(4-Hexyloxybenzoyloxy)-2,3-difluorobenzonitrile
4-(4-Heptyloxybenzoyloxy)-2,3-difluorobenzonitrile
4-(4-Octyloxybenzoyloxy)-2,3-difluorobenzonitrile
4-(4-(2-Methylbutyl)-benzoyloxy)-2,3-difluorobenzonitrile
4-(4-Acetoxybenzoyloxy)-2,3-difluorobenzonitrile
4-(4-Propionyloxybenzoyloxy)-2,3-difluorobenzonitrile
4-(4-Butyryloxybenzoyloxy)-2,3-difluorobenzonitrile
4-(4-Pentanoyloxybenzoyloxy)-2,3-difluorobenzonitrile
4-(4-Hexanoyloxybenzoyloxy)-2,3-difluorobenzonitrile
4-(4-Heptanoyloxybenzoyloxy)-2,3-difluorobenzonitrile
4-(4-Octanoyloxybenzoyloxy)-2,3-difluorobenzonitrile.

The following are obtained analogously using 4-alkylbiphenyl-4'-carboxylic acids as starting materials:
4-(4-Ethylbiphenyl-4'-ylcarbonyloxy)-2,3-difluorobenzonitrile
4-(4-Propylbiphenyl-4'-ylcarbonyloxy)-2,3-difluorobenzonitrile
4-(4-Butylbiphenyl-4'-ylcarbonyloxy)-2,3-difluorobenzonitrile
4-(4-Pentylbiphenyl-4'-ylcarbonyloxy)-2,3-difluorobenzonitrile
4-(4-Hexylbiphenyl-4'-ylcarbonyloxy)-2,3-difluorobenzonitrile
4-(4-Heptylbiphenyl-4'-ylcarbonyloxy)-2,3-difluorobenzonitrile
4-(4-Octylbiphenyl-4'-ylcarbonyloxy)-2,3-difluorobenzonitrile
4-(4-Ethoxybiphenyl-4'-ylcarbonyloxy)-2,3-difluorobenzonitrile
4-(4-Propoxybiphenyl-4'-ylcarbonyloxy)-2,3-difluorobenzonitrile
4-(4-Butoxybiphenyl-4'-ylcarbonyloxy)-2,3-difluorobenzonitrile
4-(4-Pentoxybiphenyl-4'-ylcarbonyloxy)-2,3-difluorobenzonitrile
4-(4-Hexyloxybiphenyl-4'-ylcarbonyloxy)-2,3-difluorobenzonitrile
4-(4-Heptyloxybiphenyl-4'-ylcarbonyloxy)-2,3-difluorobenzonitrile
4-(4-Octyloxybiphenyl-4'-ylcarbonyloxy)-2,3-difluorobenzonitrile
4-(4-(2-Methylbutyl)-biphenyl-4'-ylcarbonyloxy)-2,3-difluorobenzonitrile.

The following are obtained analogously using 4-(trans-4-alkylcyclohexyl)-benzoic acids as starting materials:
4-(4-(trans-4-Ethylcyclohexyl)-benzoyloxy)-2,3-difluorobenzonitrile
4-(4-trans-4-Propylcyclohexyl)-benzoyloxy)-2,3-difluorobenzonitrile, K 98° N195° I
4-(4-(trans-4-Butylcyclohexyl)-benzoyloxy)-2,3-difluorobenzonitrile
4-(4-(trans-4-Pentylcyclohexyl)-benzoyloxy)-2,3-difluorobenzonitrile
4-(4-(trans-4-Hexylcyclohexyl)-benzoyloxy)-2,3-difluorobenzonitrile
4-(4-(trans-4-Heptylcyclohexyl)-benzoyloxy)-2,3-difluorobenzonitrile
4-(4-(trans-Octylcyclohexyl)-benzoyloxy)-2,3-difluorobenzonitrile
4-(4-(trans-4-Ethoxycyclohexyl)-benzoyloxy)-2,3-difluorobenzonitrile
4-(4-(trans-4-Propoxycyclohexyl)-benzoyloxy)-2,3-difluorobenzonitrile
4-(4-trans-4-Butoxycyclohexyl)-benzoyloxy)-2,3-difluorobenzonitrile
4-(4-(trans-4-Pentoxycyclohexyl)-benzoyloxy)-2,3-difluorobenzonitrile
4-(4-(trans-Hexyloxycyclohexyl)-benzoyloxy)-2,3-difluorobenzonitrile
4-(4-(trans-4-Heptyloxycyclohexyl)-benzoyloxy)-2,3-difluorobenzonitrile
4-(4-(trans-4-Octyloxycyclohexyl)-benzoyloxy)-2,3-difluorobenzonitrile.

The following are obtained analogously using 4-(5-alkyldioxan-2-yl)-benzoic acids as starting materials:
4-(4-(5-Ethyldioxan-2-yl)-benzoyloxy)-2,3-difluorobenzonitrile
4-(4-(5-Propyldioxan-2-yl)-benzoyloxy)-2,3-difluorobenzonitrile
4-(4-(5-Butyldioxan-2-yl)-benzoyloxy)-2,3-difluorobenzonitrile
4-(4-(5-Pentyldioxan-2-yl)-benzoyloxy)-2,3-difluorobenzonitrile
4-(4-(5-Hexyldioxan-2-yl)-benzoyloxy)-2,3-difluorobenzonitrile
4-(4-(5-Heptyldioxan-2-yl)-benzoyloxy)-2,3-difluorobenzonitrile
4-(4-(5-Octyldioxan-2-yl)-benzoyloxy)-2,3-difluorobenzonitrile
4-(4-(5-Ethoxydioxan-2-yl)-benzoyloxy)-2,3-difluorobenzonitrile
4-(4-(5-Propoxydioxan-2-yl)-benzoyloxy)-2,3-difluorobenzonitrile
4-(4-(5-Butoxydioxan-2-yl)-benzoyloxy)-2,3-difluorobenzonitrile
4-(4-(5-Pentoxydioxan-2-yl)-benzoyloxy)-2,3-difluorobenzonitrile
4-(4-(5-Hexyloxydioxan-2-yl)-benzoylozy)-2,3-difluorobenzonitrile
4-(4-(5-Heptyloxydioxan-2-yl)-benzoyloxy)-2,3-difluorobenzonitrile
4-(4-(5-Octyloxydioxan-2-yl)-benzoyloxy)-2,3-difluorobenzonitrile.

The following are obtained analogously using 4-(4-alkylbenzoyloxy)-benzoic acids as starting materials:
4-(4-(4-Ethylbenzoyloxy)-benzoyloxy)-2,3-difluorobenzonitrile
4-(4-(4-Propylbenzoyloxy)-benzoyloxy)-2,3-difluorobenzonitrile
4-(4-(4-Butylbenzoyloxy)-benzoyloxy)-2,3-difluorobenzonitrile
4-(4-(4-Pentylbenzoyloxy)-benzoyloxy)-2,3-difluorobenzonitrile
4-(4-(4-Hexylbenzoyloxy)-benzoyloxy)-2,3-difluorobenzonitrile
4-(4-(4-Heptylbenzoyloxy)-benzoyloxy)-2,3-difluorobenzonitrile
4-(4-(4-Hexylbenzoyloxy)-benzoyloxy)-2,3-difluorobenzonitrile
4-(4-(4-Ethoxybenzoyloxy)-benzoyloxy)-2,3-difluorobenzonitrile
4-(4-(4-Propoxybenzoyloxy)-benzoyloxy)-2,3-difluorobenzonitrile
4-(4-(4-Butoxybenzoyloxy)-benzoyloxy)-2,3-difluorobenzonitrile
4-(4-(4-Pentoxybenzoyloxy)-benzoyloxy)-2,3-difluorobenzonitrile 4-(4-(4-Hexyloxybenzoyloxy)-benzoyloxy)-2,3-difluorobenzonitrile
4-(4-(4-Heptyloxybenzoyloxy)-benzoyloxy)-2,3-difluorobenzonitrile
4-(4-(4-Octyloxybenzoyloxy)-benzoyloxy-2,3-difluorobenzonitrile.

The following are obtained analogously using 4-(4-(trans-4-alkylcyclohexanecarbonyloxy)-benzoic acids as starting materials:
4-(4-(trans-4-Ethylcyclohexanecarbonyloxy)-benzoyloxy)-2,3-difluorobenzonitrile
4(4(trans-4-Propylcyclohexanecarbonyloxy)-benzoyloxy)-2,3-difluorobenzonitrile
4-(4-(trans-4-Butylcyclohexanecarbonyloxy)-benzoyloxy)-2,3-difluorobenzonitrile
4-(4-(trans-4-Pentylcyclohexanecarbonyloxy)-benzoyloxy)-2,3-difluorobenzonitrile
4-(4-(trans-4-Hexylcyclohexanecarbonyloxy)-benzoyloxy)-2,3-difluorobenzonitrile
4-(4-(trans-4-Heptylcyclohexanecarbonyloxy)-benzoyloxy)-2,3-difluorobenzonitrile
4-(4-(trans-4-Octylcyclohexanecarbonyloxy)-benzoyloxy)-2,3-difluorobenzonitrile
4-(4-(trans-4-Ethoxycyclohexanecarbonyloxy)-benzoyloxy)-2,3-difluorobenzonitrile
4-(4-(trans-4-Propoxycyclohexanecarbonyloxy)-benzoyloxy)-2,3-difluorobenzonitrile
4-(4-(trans-4-Butoxycyclohexanecarbonyloxy)-benzoyloxy)-2,3-difluorobenzonitrile
4-(4-(trans-4-Pentoxycyclohexanecarbonyloxy)-benzoyloxy)-2,3-difluorobenzonitrile
4-(4-(trans-4-Hexyloxycyclohexanecarbonyloxy)-benzoyloxy)-2,3-difluorobenzonitrile
4-(4-(trans-3-Heptyloxycyclohexanecarbonyloxy)-benzoyloxy)-2,3-difluorobenzonitrile
4-(4-(trans-4-Octyloxycyclohexanecarbonyloxy)-benzoyloxy)-2,3-difluorobenzonitrile.

EXAMPLE 3

Preparation of 4-cyclohexanecarbonyloxy-2,3-difluorobenzonitriles

A mixture of 0.1 mole of trans-4-octylcyclohexanecarbonyl chloride (prepared from the carboxylic acid with oxalyl chloride in toluene) and 75 ml of methylene dichloride is added to a mixture of 0.1 mole of 2,3-difluoro-4-cyanophenol (prepared as in Example 1), 0.12 mole of pyridine, 10 mmole of 4-N,N-dimethylaminopyridine and 250 ml of methylene dichloride. After being stirred for 10 hours at room temperature, the mixture is washed with dilute hydrochloric acid, saturated sodium bicarbonate solution and water. Working up in the customary manner gives 4-(trans-4-octylcyclohexanecarbonyloxy)-2,3-difluorobenzonitrile.

The following are prepared analogously:
4-(trans-4-Ethylcyclohexanecarbonyloxy)-2,3-difluorobenzonitrile
4-(trans-4-Propylcyclohexanecarbonyloxy)-2,3-difluorobenzonitrile
4-(trans-4-Butylcyclohexanecarbonyloxy)-2,3-difluorobenzonitrile
4-(trans-4-Pentylcyclohexanecarbonyloxy)-2,3-difluorobenzonitrile
4-(trans-4-Hexylcyclohexanecarbonyloxy)-2,3-difluorobenzonitrile
4-(trans-4-Heptylcyclohexanecarbonyloxy)-2,3-difluorobenzonitrile
4-(trans-4-Ethoxycyclohexanecarbonyloxy)-2,3-difluorobenzonitrile
4-(trans-4-Propoxycyclohexanecarbonyloxy)-2,3-difluorobenzonitrile
4-(trans-4-Butoxycyclohexanecarbonyloxy)-2,3-difluorobenzonitrile
4-(trans-4-Pentoxycyclohexanecarbonyloxy)-2,3-difluorobenzonitrile
4-(trans-4-Hexyloxycyclohexanecarbonyloxy)-2,3-difluorobenzonitrile
4-(trans-4-Heptyloxycyclohexanecarbonyloxy)-2,3-difluorobenzonitrile
4-(trans-4-Octyloxycyclohexanecarbonyloxy)-2,3-difluorobenzonitrile.

The following are obtained analogously using trans, trans-4-alkylbicyclohexane-4'-carbonyl chlorides as starting materials:
4-(trans,trans-4-Ethylbicyclohexyl-4'-carbonyloxy)-2,3-difluorobenzonitrile
4-(trans,trans-4-Propylbicyclohexyl-4'-carbonyloxy)-2,3-difluorobenzonitrile
4-(trans,trans-4-Butylbicyclohexyl-4'-carbonyloxy)-2,3-difluorobenzonitrile
4(trans,trans-4-Pentylbicyclohexyl-4'-carbonyloxy)-2,3-difluorobenzonitrile
4-(trans,trans-4-Hexylbicyclohexyl-4'-carbonyloxy))-2,3-difluorobenzonitrile
4-(trans,trans-4-Heptylbicyclohexyl-4'-carbonyloxy)-2,3-difluorobenzonitrile
4-(trans,trans-4-Octylbicyclohexyl-4'-carbonyloxy)-2,3-difluorobenzonitrile
4-(trans,trans-4-Ethoxybicyclohexyl-4'-carbonyloxy)-2,3-difluorobenzonitrile
4-(trans,trans-4-Propoxybicyclohexyl-4'-carbonyloxy)-2,3-difluorobenzonitrile
4-(trans,trans-4-Butoxybicyclohexyl-4'-carbonyloxy)-2,3-difluorobenzonitrile
4-(trans,trans-4-Pentoxybicyclohexyl-4'-carbonyloxy)-2,3-difluorobenzonitrile
4-(trans,trans-4-Hexyloxybicyclohexyl-4'-carbonyloxy)-2,3-difluorobenzonitrile
4-(trans,trans-4-Heptyloxybicyclohexyl-4'-carbonyloxy)-2,3-difluorobenzonitrile
4-(trans,trans-4-Octyloxybicyclohexyl-4'-carbonyloxy)-2,3-difluorobenzonitrile.

The following are obtained analogously using trans-4-(4-alkylphenyl)-cyclohexanecarbonyl chlorides as starting materials:
4-(trans-4-(4-Ethylphenyl)-cyclohexanecarbonyloxy)-2,3-difluorobenzonitrile
4-(trans-4-(4-Propylphenyl)-cyclohexanecarbonyloxy)-2,3-difluorobenzonitrile
4-(trans-4-(4-Butylphenyl)-cyclohexanecarbonyloxy)-2,3-difluorobenzonitrile
4-(trans-4-(4-Pentylphenyl)-cyclohexanecarbonyloxy)-2,3-difluorobenzonitrile
4-(trans-4-(4-Hexylphenyl)-cyclohexanecarbonyloxy)-2,3-difluorobenzonitrile
4-(trans-4-(4-Heptylphenyl)-cyclohexanecarbonyloxy)-2,3-difluorobenzonitrile
4-(trans-4-(4-Octylphenyl)-cyclohexanecarbonyloxy)-2,3-difluorobenzonitrile
4-(trans-4-(4-Ethoxyphenyl)-cyclohexanecarbonyloxy)-2,3-difluorobenzonitrile
4-(trans-4-(4-Propoxyphenyl)-cyclohexanecarbonyloxy)-2,3-difluorobenzonitrile
4-(trans-4-(4-Butoxyphenyl)-cyclohexanecarbonyloxy)-2,3-difluorobenzonitrile 4-(trans-4-(4-Pentoxyphenyl)-cyclohexanecarbonyloxy)-2,3-difluorobenzonitrile
4-(trans-4-(4-Hexyloxyphenyl)-cyclohexanecarbonyloxy)-2,3-difluorobenzonitrile
4-(trans-4-(4-Heptyloxyphenyl)-cyclohexanecarbonyloxy)-2,3-difluorobenzonitrile
4-(trans-4-(4-Octyloxyphenyl)-cyclohexanecarbonyloxy)-2,3-difluorobenzonitrile.

The following are obtained analogously using trans-4-(2-(trans-4-alkylcyclohexyl)-ethyl)-cyclohexanecarboxylic acids as starting materials:
4-(trans-4-(2-(trans-4-Ethylcyclohexyl)-ethyl)-cyclohexanecarbonyloxy)-2,3-difluorobenzonitrile
4-(trans-4-(2-(trans-4-Propylcyclohexyl)-ethyl)-cyclohexanecarbonyloxy)-2,3-difluorobenzonitrile
4-(trans-4-(2-(trans-4-Butylcyclohexyl)-ethyl)-cyclohexanecarbonyloxy)-2,3-difluorobenzonitrile
4-(trans-4-(2-(trans-4-Pentylcyclohexyl)-ethyl)-cyclohexanecarbonyloxy)-2,3-difluorobenzonitrile
4-(trans-4-(2-(trans-4-Hexylcyclohexyl)-ethyl)-cyclohexanecarbonyloxy)-2,3-difluorobenzonitrile
4-(trans-4-(2-(trans-4-Heptylcyclohexyl)-ethyl)-cyclohexanecarbonyloxy)-2,3-difluorobenzonitrile
4-(trans-4-(2-(trans-4-Octylcyclohexyl)-ethyl)-cyclohexanecarbonyloxy)-2,3-difluorobenzonitrile.

EXAMPLE 4

Preparation of 4-benzyloxy-2,3-difluorobenzonitriles

A mixture of 0.12 mole of p-pentylbenzyl chloride and 20 ml of ethanol is added to a mixture of 0.1 mole of 2,3-difluoro-4-cyanophenol (prepared as in Example 1) and 0.1 mole of sodium ethoxide in 60 ml of ethanol, and the mixture is heated at the boil for 5 hours. After the ethanol has been distilled off, the reaction mixture is allowed to cool and is poured onto 15 ml of 5% aqueous sodium hydroxide solution. Working up in the customary manner gives 4-(4-pentylbenzyloxy)-2,3-difluorobenzonitrile.

The following are prepared analogously:
4-(4-Ethylbenzyloxy)-2,3-difluorobenzonitrile
4-(4-Propylbenzyloxy)-2,3-difluorobenzonitrile
4-(4-Butylbenzyloxy)-2,3-difluorobenzonitrile
4-(4-Hexylbenzyloxy)-2,3-difluorobenzonitrile
4(4-Heptylbenzyloxy)-2,3-difluorobenzonitrile
4-(4-Octylbenzyloxy)-2,3-difluorobenzonitrile
4(4-Ethoxybenzyloxy)-2,3-difluorobenzonitrile
4-(4-Propoxybenzyloxy)-2,3-difluorobenzonitrile
4-(4-Butoxybenzyloxy)-2,3-difluorobenzonitrile
4-(4-Pentoxybenzyloxy)-2,3-difluorobenzonitrile
4-(4-Hexyloxybenzyloxy)-2,3-difluorobenzonitrile
4-(4-Heptyloxybenzyloxy)-2,3-difluorobenzonitrile
4-(4-Octyloxybenzyloxy)-2,3-difluorobenzonitrile
4-(4-Ethylbiphenyl-4'-ylmethoxy)-2,3-difluorobenzonitrile
4-(4-Propylbiphenyl-4'-ylmethoxy)-2,3-difluorobenzonitrile
4-(4-Butylbiphenyl-4'-ylmethoxy-2,3-difluorobenzonitrile
4-(4-Pentylbiphenyl-4'-ylmethoxy)-2,3-difluorobenzonitrile
4-(4-Hexylbiphenyl-4'-ylmethoxy)-2,3-difluorobenzonitrile
4-(4-Heptylbiphenyl-4'-ylmethoxy)-2,3-difluorobenzonitrile
4-(4-Octylbiphenyl-4'-ylmethoxy)-2,3-difluorobenzonitrile
4-(4-Ethoxybiphenyl-4'-ylmethoxy)-2,3-difluorobenzonitrile
4-(4-Propoxybiphenyl-4'-ylmethoxy)-2,3-difluorobenzonitrile
4-(4-Butoxybiphenyl-4'-ylmethoxy)-2,3-difluorobenzonitrile
4-(4-Pentoxybiphenyl-4'-ylmethoxy)-2,3-difluorobenzonitrile
4-(4-Hexyloxybiphenyl-4'-ylmethoxy)-2,3-difluorobenzonitrile
4-(4-Heptyloxybiphenyl-4'-ylmethoxy)-2,3-difluorobenzonitrile
4-(4-Octyloxybiphenyl-4'-ylmethoxy)-2,3-difluorobenzonitrile
4-(4-(trans-4-Ethylcyclohexyl)-benzyloxy)-2,3-difluorobenzonitrile
4-(4-(trans-4-Propylcyclohexyl)-benzyloxy)-2,3-difluorobenzonitrile
4-(4-(trans-4-Butylcyclohexyl)-benzyloxy)-2,3-difluorobenzonitrile
4-(4-(trans-4Pentylcyclohexyl)-benzyloxy)-2,3-difluorobenzonitrile
4-(4-(trans-4Hexylcyclohexyl)-benzyloxy)-2,3-difluorobenzonitrile
4-(4-(trans-4-Heptylcyclohexyl)-benzyloxy)-2,3-difluorobenzonitrile
4-(4-(trans-4-Octylcyclohexyl)-benzyloxy)-2,3-difluorobenzonitrile
4-(4-(trans-4-Ethoxycyclohexyl)-benzyloxy)-2,3-difluorobenzonitrile
4-(4-(trans-4-Propoxycyclohexyl)-benzyloxy)-2,3-difluorobenzonitrile
4-(4-(trans-4-Butoxycyclohexyl)-benzyloxy)-2,3-difluorobenzonitrile
4-(4-(trans-4-Pentoxycyclohexyl)-benzyloxy)-2,3-difluorobenzonitrile
4-(4-(trans-4-Hexyloxycyclohexyl)-benzyloxy)-2,3-difluorobenzonitrile
4-(4-(trans-4-Heptyloxycyclohexyl)-benzyloxy)-2,3-difluorobenzonitrile
4-(4-(trans-4-Octyloxycyclohexyl)-benzyloxy)-2,3-difluorobenzonitrile
4-(4-(5-Ethyldioxan-2-yl)-benzyloxy)-2,3-difluorbenzonitrile
4-(4-(5-Propyldioxan-2-yl)-benzyloxy)-2,3-difluorobenzonitrile
4-(4-(5-Butyldioxan-b 2-yl)-benzyloxy)-2,3-difluorobenzonitrile
4-(4-(5-Pentyldioxan-2-yl)-benzyloxy)-2,3difluorbenzontrile
4-(4-(5-Hexyldioxan-2-yl)-benzyloxy)-2,3-difluorobenzonitrile
4-(4-(5-Heptyldioxan-2-yl)-benzyloxy)-2,3-difluorobenzonitrile
4-(4-(5-Octyldioxan-2-yl)-benzyloxy)-2,3-difluorobenzonitrile
4-(4-(5-Ethoxydioxan-2-yl)-benzyloxy)-2,3-difluorobenzonitrile
4-(4-(5-Butoxydioxan-2-yl)-benzyloxy)-2,3-difluorobenzonitrile
4-(4-(5-Pentoxydioxan-2-yl)-benzyloxy)-2,3-difluorobenzonitrile
4-(4-(5-Hexyloxydioxan-2-yl)-benzyloxy)-2,3-difluorobenzonitrile
4-(4-(5-Heptyloxydioxan-2-yl)-benzyloxy)-2,3-difluorobenzonitrile
4-(4-(5-Octyloxydioxan-2-yl)-benzyloxy)-2,3-difluorobenzonitrile 4-(4-(5-Ethylpyrimidin-2-yl)-benzyloxy)-2,3-difluorobenzonitrile
4-(4-(5-Propylpyrimidin-2-yl)-benzyloxy)-2,3-difluorobenzonitrile
4-(4-(5-Butylpyrimidin-2-yl)-benzyloxy)-2,3-difluorobenzonitrile
4-(4-(5-(Pentylpyrimidin-2-yl)-benzyloxy)-2,3-difluorobenzonitrile
4-(4-(5-Hexylpyrimidin-2-yl)-benzyloxy)-2,3-difluorobenzonitrile
4-(4-(5-Heptylpyrimidin-2-yl)-benzyloxy)-2,3-difluorobenzonitrile
4-(4-(5-Octylpyrimidin-2-yl)-benzyloxy)-2,3-difluorobenzonitrile
4-(4-(5-Ethoxypyrimidin-2-yl)-benzyloxy)-2,3-difluorobenzonitrile
4-(4-(5-Propoxypyrimidin-2-yl)-benzyloxy)-2,3-difluorobenzonitrile
4-(4-(5-Butoxypyrimidin-2-yl)-benzyloxy)-2,3-difluorobenzonitrile
4-(4-(5-Pentoxypyrimidin-2-yl)-benzyloxy)-2,3-difluorobenzonitrile
4-(4-(5-Hexyloxypyrimidin-2-yl)-benzyloxy)-2,3-difluorobenzonitrile
4-(4-(5-Heptyloxypyrimidin-2-yl)-benzyloxy)-2,3-difluorobenzonitrile
4-(4-(5-Octyloxypyrimidin-2-yl)-benzyloxy)-2,3-difluorobenzonitrile

EXAMPLE 5

Preparation of 4-(cyclohexylmethoxy)-2,3-difluorobenzonitriles 0.1 mole of 1-(trans-4pentylcyclohexyl-1-methoxy)-2,3-difluorobenzene (prepared from 2,3-difluorophenol and trans-4-pentylcyclohexylmethyl iodide analogously to Example 4) is deprotonated by means of n-butyllithium in tetrahydrofuran/tetramethylethylenediamine and is formylated by means of N-formylpiperidine. The formyl compound is reacted as in Example 1b) with hydroxylamine-O-sulfonic acid. Working up in the customary manner gives 4-(trans-4-pentylcyclohexylmethoxy)-2,3-difluorobenzonitrile.

The following are obtained analogously:
4-(trans-4-Ethylcyclohexylmethoxy)-2,3-difluorobenzonitrile
4-(trans-4-Propylcyclohexylmethoxy)-2,3-difluorobenzonitrile
4-(trans-4-Butylcyclohexylmethoxy)-2,3-difluorobenzonitrile 4-(trans-4-Hexylcyclohexylmethoxy)-2,3-difluorobenzonitrile
4-(trans-4-Heptylcyclohexylmethoxy)-2,3-difluorobenzonitrile
4-(trans-4-Octylcyclohexylmethoxy)-2,3-difluorobenzonitrile
4-(trans-4-Ethoxycyclohexylmethoxy)-2,3-difluorobenzonitrile
4-(trans-4-Propoxycyclohexylmethoxy)-2,3-difluorobenzonitrile
4-(trans-4-Butoxycyclohexylmethoxy)-2,3-difluorobenzonitrile
4-(trans-4-Pentoxycyclohexylmethoxy)-2,3-difluorobenzonitrile
4-(trans-4-Hexyloxycyclohexylmethoxy)-2,3-difluorobenzonitrile
4-(trans-4-Heptyloxycyclohexylmethoxy)-2,3-difluorobenzonitrile
4-(trans-4-Octyloxycyclohexylmethoxy)-2,3-difluorobenzonitrile
4-(trans,trans-4-Ethylbicyclohexyl-4'-methoxy)-2,3-difluorobenzonitrile
4-(trans,trans-4-Propylbicyclohexyl-4'-methoxy)-2,3-difluorobenzonitrile
4-(trans,trans,-4-Butylbicyclohexyl-4'-methoxy)-2,3-difluorobenzonitrile
4-(trans,trans-4-Pentylbicyclohexyl-4'-methoxy)-2,3-difluorobenzonitrile
4-(trans,trans-4-Hexylbicyclohexyl-4'-methoxy)-2,3-difluorobenzonitrile
4-(trans,trans-4-Heptylbicyclohexyl-4'-methoxy)-2,3-difluorobenzonitrile
4-(trans,trans-4-Octylbicyclohexyl-4'-methoxy)-2,3-difluorobenzonitrile
4-(trans,trans-4-Ethoxybicyclohexyl-4'-methoxy)-2,3-difluorobenzonitrile
4-(trans,trans-4-Propoxybicyclohexyl-4'-methoxy)-2,3-difluorobenzonitrile
4-(trans,trans-4-Butoxybicyclohexyl-4'-methoxy)-2,3-difluorobenzonitrile
4-(trans,trans-4-Pentoxybicyclohexyl-4'-methoxy)-2,3-difluorobenzonitrile
4-(trans,trans-4-Hexyloxybicyclohexyl-4'-methoxy)-2,3-difluorobenzonitrile
4-(trans,trans-4-Heptyloxycyclohexyl-4'-methoxy)-2,3-difluorobenzonitrile
4-(trans,trans-4-Octyloxybicyclohexyl-4'-methoxy)-2,3-difluorobenzonitrile
4-(trans,-4-(4-Ethylphenyl)-cyclhexylmethoxy)-2,3-difluorobenzonitrile
4-(trans-4-(4-Propylphenyl)-cyclohexymethoxy)-2,3-difluorobenzonitrile
4-(trans-4-(4-butylphenyl)-cyclohexylmethoxy)-2,3-difluorobenzonitrile
4-(trans-4-(4-Pentylphenyl)-cyclohexylmethoxy)-2,3-difluorobenzonitrile
4-(trans-4-(4-Hexylphenyl)-cyclohexylmethoxy)-2,3-difluorobenzonitrile
4-(trans-4-(4-Heptylphenyl)-cyclohexylmethoxy)-2,3-difluorobenzonitrile
4-(trans-4-(4-Octyphenyl)-cyclohexylmethoxy)-2,3-difluorobenzonitrile
4-(trans-4-(4-Ethoxyphenyl)-cyclohexylmethoxy)-2,3-difluorobenzonitrile
4-(trans-4-(4-Propoxyphenyl)-cyclohexylmethoxy)-2,3-difluorobenzonitrile
4-(trans-4-(4-Butoxyphenyl)-cyclohexylmethyoxy)-2,3,-difluorobenzonitrile
4-(trans-4-(4-Pentoxyphenyl)-cyclohexylmethoxy)-2,3-difluorobenzonitrile
4-(trans-4-(4-Hexyloxyphenyl)-cyclohexylmethoxy)-2,3-difluorobenzonitrile
4-(trans-4-(4-Heptyloxyphenyl)-cyclohexylmethoxy)-2,3-difluorobenzonitrile
4-(trans-4-(4-Octyloxyphenyl)-cyclohexylmethoxy)-2,3-difluorobenzonitrile.

EXAMPLE A

A liquid crystal medium is formulated consisting of
21,6% 4-(trans-4-propylcyclohexyl)-benzonitrile
32,4% 4-(trans-4-pentylcyclohexyl)-benzonitrile
22,5% 4-(trans-4-heptylcyclohexyl)-benzonitrile
13,5% 4-(trans-4-pent ylcyclohexyl)-4'-cyanobiphenyle
and
10% 4-(4-(trans-4-propylcyclohexyl)-benzoyloxy-2,3-difluorobenzonitrile clearing point: 76,9° C., Δn 0,1433.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A derivative of 4-cyano-2,3-difluorphenol of the formula

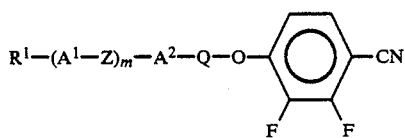

wherein
$R^1$ is $C_{1-12}$-alkyl or $C_{1-12}$-alkyl wherein one or two $CH_2$ groups are replaced by at least one of —O—, —CO—, —CO—O—, or —CH=CH—, where two O atoms are not directly attached to one another, $A^1$ and $A^2$ are each independently 1,4-phenylene; 1,4-phenylene substituted by one or two F atoms; 1,4-phenylene or 1,4-phenylene substituted by 1 to 2 F atoms in which one or two CH groups are replaced by N; trans-1,4-cyclohexylene; or trans-1,4-cyclohexylene in which one or two non-adjacent $CH_2$ groups are replaced by O atoms, S atoms, or both, Z is —CO—O—, —O—CO—, —CH$_2$CH$_2$—, OCH$_2$—, —CH$_2$O—, —C≡C— or a single bond, m is 0, 1 or 2 and Q is —CO— or —CH$_2$—.

2. A compound according to claim 1, wherein $R^1$ is alkyl or alkoxy.

3. A compound according to claim 1, wherein $A^1$ and $A^2$ are each independently PheX, Cyc, Phe, Dio or Pyr and wherein PheX is a group of the formula

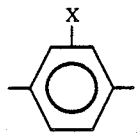

Cyc is a 1,4-cyclohexylene group, Phe is a 1,4-phenylene group, Dio is a 1,3-dioxane-2,5-diyl group, and Pyr is a pyrimidine-2,5-diyl group.

4. A compound according to claim 1, wherein m is 1.

5. A compound according to claim 1, wherein each Z is independently —CO—O—, —O—CO—, —C≡C— or —CH$_2$CH$_2$—.

6. A compound according to claim 1, wherein Z is a single bond.

7. A compound according to claim 1, wherein $R^1$ is $C_{2-10}$-alkyl or $C_{2-10}$-alkyl wherein one or two $CH_2$ groups are replaced by at least one of —O—, —CO—, —CO—O— or —CH=CH—.

8. In a liquid crystalline phase comprising at least two liquid crystal components, the improvement wherein at least one component is a compound of claim 1.

9. In a liquid crystalline display element comprising a liquid crystalline phase, the improvement wherein the liquid crystalline phase is one according to claim 8.

10. In a electrooptical display element comprising a liquid crystalline dielectric, the improvement wherein the dielectric is a phase according to claim 10.

11. In a liquid crystal phase comprising at least two liquid crystal components, the improvement wherein at least one component is a compound of claim 1, whereby said phase has a low ratio of Δε/ε1.

* * * * *